(12) United States Patent
Herzinger et al.

(10) Patent No.: US 6,795,184 B1
(45) Date of Patent: Sep. 21, 2004

(54) ODD BOUNCE IMAGE ROTATION SYSTEM IN ELLIPSOMETER SYSTEMS

(75) Inventors: Craig M. Herzinger, Lincoln, NE (US); Steven E. Green, Lincoln, NE (US); Blaine D. Johs, Lincoln, NE (US)

(73) Assignee: J.A. Woollam Co., INC, Lincoln, NE (US)

( * ) Notice: Subject to any disclaimer, the term of this patent is extended or adjusted under 35 U.S.C. 154(b) by 536 days.

(21) Appl. No.: 09/963,573

(22) Filed: Sep. 26, 2001

Related U.S. Application Data
(60) Provisional application No. 60/281,706, filed on Apr. 6, 2001.

(51) Int. Cl.$^7$ .............................................. G01J 4/00
(52) U.S. Cl. ................. 356/369; 356/364; 356/365; 356/368
(58) Field of Search ................. 356/364, 365, 356/366, 367, 368, 369, 445; 250/225; 359/487, 833, 834, 488, 599, 613, 614, 496, 497

(56) References Cited

U.S. PATENT DOCUMENTS

| | | | |
|---|---|---|---|
| 4,210,401 A | 7/1980 | Batten | 356/369 |
| 4,332,476 A | 6/1982 | Stenberg et al. | 356/369 |
| 4,355,903 A | 10/1982 | Sandercock | 356/382 |
| 4,373,817 A | 2/1983 | Coates | 356/384 |
| 4,647,207 A | 3/1987 | Bjork et al. | 356/369 |
| 4,681,450 A * | 7/1987 | Azzam | 356/367 |
| 4,750,822 A | 6/1988 | Rosencwaig et al. | 356/445 |
| 4,826,321 A | 5/1989 | Coates et al. | 356/351 |
| 4,838,695 A | 6/1989 | Mansuripur et al. | 356/369 |
| 5,042,951 A | 8/1991 | Gold et al. | 356/369 |
| 5,045,704 A | 9/1991 | Coates | 250/372 |
| RE34,783 E | 11/1994 | Coates | 250/372 |
| 5,373,359 A | 12/1994 | Woollam et al. | 356/328 |
| 5,452,091 A | 9/1995 | Johnson | 356/445 |
| 5,504,582 A | 4/1996 | Johs et al. | 356/369 |
| 5,521,706 A | 5/1996 | Green et al. | 356/369 |
| 5,596,406 A | 1/1997 | Rosencwaig et al. | 356/327 |
| 5,666,201 A | 9/1997 | Johs et al. | 356/369 |
| 5,706,212 A | 1/1998 | Thompson et al. | 364/525 |
| 5,757,494 A | 5/1998 | Green et al. | 356/369 |
| 5,872,630 A | 2/1999 | Johs et al. | 356/369 |
| 5,929,995 A * | 7/1999 | Johs | 356/369 |
| 5,946,098 A | 8/1999 | Johs et al. | 356/364 |
| 5,956,145 A | 9/1999 | Green et al. | 356/364 |
| 5,963,325 A | 10/1999 | Johs et al. | 356/364 |
| 5,963,327 A | 10/1999 | He et al. | 356/369 |
| 6,084,674 A | 7/2000 | Johs et al. | 356/364 |
| 6,084,675 A * | 7/2000 | Herzinger et al. | 356/369 |
| 6,100,981 A | 8/2000 | Johs et al. | 356/364 |
| 6,118,537 A | 9/2000 | Johs et al. | 356/369 |
| 6,137,618 A | 10/2000 | Herzinger | 359/245 |
| 6,141,102 A | 10/2000 | Johs et al. | 356/364 |

OTHER PUBLICATIONS

"Regression Calibration Method for Rotating Element Ellipsmeters", Johs, Thin Solid Films, 234 (1993).
"An Automated Scanning Ellipsometer", Smith, Surface Science, vol. 56, No. 1, (1976).
"Automatic Rotating Element Ellipsometers: Calibration, Operation and Real-Time Applications", Collins, Rev. Sci. Instrum., 61(8) (1990).

\* cited by examiner

*Primary Examiner*—Frank G. Font
*Assistant Examiner*—Roy M. Punnoose
(74) *Attorney, Agent, or Firm*—James D. Welch (57) ABSTRACT

Disclosed is an odd bounce image rotating system with a sequence of an odd number of reflecting elements, such that a polarized electromagnetic beam caused to enter, reflectively interacts with the odd number of reflecting elements and exits along an essentially non-deviated, non-displaced locus, but with an azimuthally rotated polarization state. Application to, and methodology of application to set azimuthal angles of polarization in spectroscopic ellipsometer, polarimeter and the like systems is also disclosed.

10 Claims, 3 Drawing Sheets

ODD BOUNCE IMAGE ROTATION SYSTEM IN ELLIPSOMETER SYSTEMS

This Application is a Continuation-In-Part of Provisional Application Serial No. 60/281,706, filed Apr. 6, 2001.

The invention in this application was developed in part under support provided by a Grant from the National Science Foundation under Phase II SBIR Contract No. 9901510. The United States Government has certain rights in this invention.

TECHNICAL FIELD

The present invention relates to polarization state modifying systems which find application in ellipsometer, polarimeter and the like systems. More particularly the present invention comprises an image rotating system comprised of a sequence of an odd number of reflecting elements, such that a linearly, or partially linearly polarized electromagnetic beam caused to enter, reflectively interacts with the odd number of reflecting elements and exits in a direction which is essentially non-deviated and non-displaced, with an azimuthally rotated, but otherwise substantially unchanged, polarization state.

BACKGROUND

The practice of ellipsometry is well established as a non-destructive approach to determining characteristics of sample systems, and can be practiced in real time. The topic is well described in a number of publications, one such publication being a review paper by Collins, titled "Automatic Rotating Element Ellipsometers: Calibration, Operation and Real-Time Applications", Rev. Sci. Instrum., 61(8) (1990).

Before proceeding, as it is relevant to the present invention, it is noted that ellipsometer systems generally comprise means for setting a linear or elliptical polarization state, (typically substantially linear).

Continuing, in general, modern practice of ellipsometry typically involves causing a spectroscopic beam of electromagnetic radiation, in a known state of polarization, to interact with a sample system at at least one angle of incidence with respect to a normal to a surface thereof, in a plane of incidence. (Note, a plane of incidence contains both a normal to a surface of an investigated sample system and the locus of said beam of electromagnetic radiation). Changes in the polarization state of said beam of electromagnetic radiation which occur as a result of said interaction with said sample system are indicative of the structure and composition of said sample system. The practice of ellipsometry further involves proposing a mathematical model of the ellipsometer system and the sample system investigated by use thereof, and experimental data is then obtained by application of the ellipsometer system. This is typically followed by application of a square error reducing mathematical regression to the end that parameters in the mathematical model which characterize the sample system are evaluated, such that the obtained experimental data, and values calculated by use of the mathematical model, are essentially the same.

A typical goal in ellipsometry is to obtain, for each wavelength in, and angle of incidence of said beam of electromagnetic radiation caused to interact with a sample system, sample system characterizing PSI and DELTA values, (where PSI is related to a change in a ratio of magnitudes of orthogonal components $r_p/r_s$ in said beam of electromagnetic radiation, and wherein DELTA is related to a phase shift entered between said orthogonal components $r_p$ and $r_s$), caused by interaction with said sample system:

$PSI=|r_p/r_s|$; and $DELTA=(\Delta r_p - \Delta r_s)$.

As alluded to, the practice of ellipsometry requires that a mathematical model be derived and provided for a sample system and for the ellipsometer system being applied. In that light it must be appreciated that an ellipsometer system which is applied to investigate a sample system is, generally, sequentially comprised of:

a. a Source of a beam electromagnetic radiation;
b. a Polarizer element;
c. optionally a compensator element;
d. (additional element(s));
e. a sample system;
f. (additional element(s));
g. optionally a compensator element;
h. an Analyzer element; and
i. a Spectroscopic Detector System.

Each of said components b.–i. must be accurately represented by a mathematical model of the ellipsometer system along with a vector which represents a beam of electromagnetic radiation provided from said source of a beam electromagnetic radiation, Identified in a. above)

Various conventional ellipsometer configurations provide that a Polarizer, Analyzer and/or Compensator(s) can be rotated during data acquisition, and are describe variously as Rotating Polarizer (RPE), Rotating Analyzer (RAE) and Rotating Compensator (RCE) Ellipsometer Systems. It is noted, that nulling ellipsometers also exist in which elements therein are rotatable in use, rather than rotating. Generally, use of a nulling ellipsometer system involves imposing a substantially linear polarization state on a beam of electromagnetic radiation with a linear polarizer, causing the resulting polarized beam of electromagnetic radiation to interact with a sample system, and then adjusting an analyzer to an azimuthal azimuthal angle which effectively cancels out the beam of electromagnetic radiation which proceeds past the sample system. The azimuthal angle of the analyzer at which nulling occurs provides insight to properties of the sample system.

Continuing, in use, data sets can be obtained with an ellipsometer system configured with a sample system present, sequentially for cases where other sample systems are present, and where an ellipsometer system is configured in a straight-through configuration wherein a beam of electromagnetic radiation is caused to pass straight through the ellipsometer system without interacting with a sample system. Simultaneous mathematical regression utilizing multiple data sets can allow calibration of ellipsometers and evaluation of sample system characterizing PSI and DELTA values over a range of wavelengths. The obtaining of numerous data sets with an ellipsometer system configured with, for instance, a sequence of sample systems present and/or wherein a sequential plurality of polarization states are imposed on an electromagnetic beam caused to interact therewith, can allow system calibration of numerous ellipsometer system variables.

Patent to Herzinger, U.S. Pat. No. 6,137,618 is disclosed as it describes a Single Brewster Angle Polarizer in the context of multiple reflecting means, and discloses prior art dual Brewster Angle Single Reflective Means Polarizer Systems.

Another Patent, to Herzinger et al., U.S. Pat. No. 6,084,675 describes an adjustable beam alignment compensator/retarder with application to spectroscopic ellipsometry.

U.S. Pat. No. 6,118,537 to Johs et al. describes a multiple Berek plate optical retarder system.

U.S. Pat. No. 6,141,102 to Johs et al. describes a single triangular shaped optical retarder element.

U.S. Pat. No. 5,946,098 to Johs et al., describes dual tipped wire grid polarizers in combination with various compensator/retarder systems.

U.S. Pat. No. 6,100,981 to Johs et al., describes a dual horizontally oriented triangular shaped optical retarder.

U.S. Pat. No. 6,084,674 to Johs et al., describes a parallelogram shaped optical retarder element.

U.S. Pat. No. 5,963,325 to Johs et al., describes a dual vertically oriented triangular shaped optical retarder element.

A Patent to Johs et al., U.S. Pat. No. 5,872,630 is disclosed as it describes an ellipsometer system in which an analyzer and polarizer are maintained in a fixed in position during data acquisition, while a compensator is caused to continuously rotate.

A Patent to Thompson et al. U.S. Pat. No. 5,706,212 is also disclosed as it teaches a mathematical regression based double Fourier series ellipsometer calibration procedure for application, primarily, in calibrating ellipsometers system utilized in infrared wavelength range. Bi-refringent, transmissive window-like compensators are described as present in the system thereof, and discussion of correlation of retardations entered by sequentially adjacent elements which do not rotate with respect to one another during data acquisition is described therein.

Further Patents of which the Inventor is aware include:

U.S. Pat. Nos. 5,757,494; and 5,956,145;

to Green et al., in which are taught a method for extending the range of Rotating Analyzer/Polarizer ellipsometer systems to allow measurement of DELTA'S near zero (0.0) and one-hundred-eighty (180) degrees, and the extension of modulator element ellipsometers to PSI'S of forty-five (45) degrees. Said Patents describes the presence of a variable, transmissive, bi-refringent component which is added, and the application thereof during data acquisition to enable the identified capability.

A Patent to He et al., U.S. Pat. No. 5,963,327 is disclosed as it describes an ellipsometer system which enables providing a polarized beam of electromagnetic radiation at an oblique angle-of-incidence to a sample system in a small spot area.

Patents of general interest of which the Inventor is aware include:

Patent to Woollam et al, U.S. Pat. No. 5,373,359;

Patent to Johs et al. U.S. Pat. No. 5,666,201;

Patent to Green et al., U.S. Pat. No. 5,521,706; and

Patent to Johs et al., U.S. Pat. No. 5,504,582;

and are disclosed as they pertain to ellipsometer systems.

A Patent to Coates et al., U.S. Pat. No. 4,826,321 is disclosed as it describes applying a reflected monochromatic beam of plane polarized electromagnetic radiation at a Brewster angle of incidence to a sample substrate to determine the thickness of a thin film thereupon. This Patent also describes calibration utilizing two sample substrates, which have different depths of surface coating.

Other Patents which describe use of reflected electromagnetic radiation to investigate sample systems are:

U.S. Pat. Nos. RE 34,783, 4,373,817, 5,045,704 to Coates; and

U.S. Pat. No. 5,452,091 to Johnson.

A Patent to Bjork et al., U.S. Pat. No. 4,647,207 is disclosed as it describes an ellipsometer system which has provision for sequentially, individually positioning a plurality of reflective polarization state modifiers in a beam of electromagnetic radiation. U.S. Pat. Nos. 4,210,401; 4,332,476 and 4,355,903 are also identified as being cited in the 207 Patent. It is noted that systems as disclosed in these Patents, (particularly in the 476 Patent), which utilize reflection from an element to modify a polarization state can, if such an element is an essential duplicate of an investigated sample and is rotated ninety degrees therefrom, the effect of the polarization state modifying element on the electromagnetic beam effect is extinguished by the sample.

A Patent to Mansuripur et al., U.S. Pat. No. 4,838,695 is disclosed as it describes an apparatus for measuring reflectivity.

Patents to Rosencwaig et al., U.S. Pat. Nos. 4,750,822 and 5,595,406 are also identified as they describe systems which impinge electromagnetic beams onto sample systems at oblique angles of incidence. The 406 Patent provides for use of multiple wavelengths and multiple angles of incidence. For similar reasons U.S. Pat. No. 5,042,951 to Gold et al. is also disclosed.

In addition to the identified Patents, certain Scientific papers are also identified.

A paper by Johs, titled "Regression Calibration Method for Rotating Element Ellipsometers", Thin Solid Films, 234 (1993) is also disclosed as it describes a mathematical regression based approach to calibrating ellipsometer systems.

A paper by Smith, titled "An Automated Scanning Ellipsometer", Surface Science, Vol. 56, No. 1. (1976), is also mentioned as it describes an ellipsometer system which does not require any moving, (eg. rotating), elements during data acquisition.

Even in view of relevant prior art, there remains need for a more convenient approach to providing linearly polarized beams of electromagnetic radiation in which the azimuthal angle of the linear polarization can be controlled. The present invention responds to said identified needs.

DISCLOSURE OF THE INVENTION

The present invention comprises an "odd bounce optical image rotating-system", and method of its application in ellipsometer and polarimeter and the like systems. The odd bounce optical image rotating system serves to rotate the azimuthal angle of a linearly, or partially linearly polarized beam of electromagnetic radiation without entering significant deviation or displacement of the propagation direction locus thereof, or significantly altering the polarization state thereof, (ie. it does not cause significant shifting of energy from a major intensity orthogonal component into the other orthogonal component, or the shifting of phase angle therebetween). The odd bounce optical image rotating system can be described as a sequence of an odd number of reflective elements oriented in a manner which causes an entering beam of electromagnetic radiation to reflect from a first thereof onto the second thereof and from the second thereof onto the third thereof etc. For a three (3) reflective element odd bounce optical image rotating element system, said three reflections cause a beam of electromagnetic radiation to emerge from the third reflective element with a rotated linear or partially linear polarization azimuthal angle and in a direction which is not significantly deviated or displaced from the locus of the input beam, even when the odd bounce optical image rotating system is caused to stepwise or continuously rotate about an axis coincident with the locus of the beam of electromagnetic radiation. The same is generally true for an odd bounce optical image rotating element system comprising any odd number, (eg. 3, 5, 7 etc.) of reflective elements. It is noted that the greater the number of reflective elements the more normal the angle of incidence a beam can make thereto, and higher angles of incidence cause less aberration effects. Also, where more than three reflection elements are present certain non-idealities caused by the reflection elements can be canceled by utilizing non-coincident coordinate systems for said reflections. A trade-off, however, is that the greater the number of reflective elements present, the more difficult it is to align the system to avoid said beam deviation and displacement.

Coupling the odd bounce optical image rotating system with a substantially linear polarizing polarizer provides a polarizer system in which the substantially linear polarizing polarizer can remain stationary while the azimuthal angle of a substantially linearly polarized beam of electromagnetism exiting therefrom, (as viewed from a position along the locus of an electromagnetic beam caused to enter thereto), is rotated.

For general insight, it is also noted that a single three-hundred-sixty (360) degree rotation of a present invention odd bounce optical image rotating element system about an axis coincident with a beam of electromagnetic radiation which functionally passes therethrough, causes seven-hundred-twenty (720) degrees of rotation of the major intensity orthogonal component. This is not of any critical consequence, but is mentioned as it must be taken into account during practice of present invention methodology.

In the context of a material system investigation system, (eg. ellipsometer, polarimeter etc.), sequentially comprising:
  source of electromagnetic radiation;
  substantially linear polarizer;
  stage for supporting a sample system analyzer; and
  detector;
the present invention teaches the presence of at least one odd bounce optical image rotating system being present between said substantially linear polarizer and said stage for supporting a sample system and/or between said stage for supporting a sample system and said analyzer, said at least one odd bounce optical image rotating system comprising an odd number of at least three reflective elements; such that a beam of electromagnetic radiation provided by said source of electromagnetic radiation, after passing through said substantially linear polarizer, interacts with a sample system place on the stage for supporting a sample system passes through said analyzer before entering said detector, said beam of electromagnetic radiation further interacting with each of said odd number of reflective elements of said at least one odd bounce optical image rotating element, and exiting therefrom along a substantially non-deviated non-displaced trajectory.

Again, the odd bounce optical image rotating system can consist of any odd number of reflective elements, with three (3) and five (5) being preferred in the practical sense.

The present invention also includes a method of obtaining data, comprising the steps of:
a. providing a system which comprises an odd bounce optical image rotating system, as described above;
b. causing a beam of electromagnetic radiation to exit said source of electromagnetic radiation, interact with said substantially linear polarizer, a sample system and said analyzer prior to entering said detector, and in addition interact with said at least one odd bounce optical image rotating element without significant change in trajectory;
c. collecting output signals from said detector.

An additional step can further comprise the step of causing the at least one odd bounce optical image rotating element to rotate, step-wise or continuously, around the locus of the trajectory of the electromagnetic beam while practicing step c. Note, where the rotation is step-wise, motion is stopped during data acquisition.

In addition, said material system investigation system, (eg. ellipsometer, polarimeter etc.), can be caused to include a rotating compensator which during use in collecting data is caused to continuously rotate about a locus of an electromagnetic beam passing therethrough, while the substantially linear polarizer and analyzer are held essentially fixed in position and the present invention odd bounce optical image rotating element is caused to be stepped through a series of rotation positions around the locus of the beam of electromagnetic radiation caused to pass therethrough, (and held motionless during data acquisition). This allows collecting data at multiple substantially linear polarization state azimuthal angle orientations, much as is typically effected by stepwise rotating a linear polarizer, (or analyzer). The benefit involved is that, especially in ellipsometer/polarimeter etc. systems which operate in the IR range of wavelengths, it can be difficult to cause rotation of a linear polarizer, (or analyzer), without adversely causing deviation of a beam of electromagnetic radiation caused to pass therethrough, or causing mis-coordination of multiple elements thereof, (ie. multiple tipped wire linear polarizer as described in U.S. Pat. No. 5,946,098). The present invention allows setting fixed substantially linear polarizer, and analyzer azimuthal orientations, and use the odd bounce optical image rotating element instead to effect different electromagnetic beam azimuthal rotation orientations.

Continuing, as mentioned, the present invention finds use in a spectroscopic ellipsometer system basically comprising:
  a source of polychromatic electromagnetic radiation;
  a substantially linear polarizer which is fixed in position during data acquisition;
  a stage for supporting a sample system;
  an analyzer which is fixed in position during data acquisition; and
  a multi-element spectroscopic detector system.
wherein the substantially linear polarizer and analyzer can be elements which include a narrow elongated slit therein, through which a beam of random polarization state electromagnetic radiation is caused to pass, to the end that it emerges therefrom as a beam of electromagnetic radiation with a linear polarization imposed thereupon. Further, the substantially linear Polarizer can be a Brewster Angle element in which only a "p" or "s" component of a beam of electromagnetic radiation caused to interact therewith near a "Brewster Angle" Angle-of-Incidence, emerges therefrom in reflection or transmission, respectively; wherein the "p" component indicates a polarization state aligned with a perpendicular to a surface of a Brewster Angle Polarizer and also in the plane of incidence of said beam, and where "s" indicates a polarization components perpendicular to the "p" component and also parallel to said surface of the Brewster Angle Polarizer". While such spectroscopic ellipsometer system can be operated with a continuously rotating polarizer or analyzer during data collection, the preferred approach is to include at least one compensator somewhere between the polarizer and analyzer which is caused to continuously rotate during data acquisition, while the polarizer and analyzer are held essentially fixed.

A basic present invention system then, can be described as comprising a functional combination of a fixed position substantially linear polarizer in combination with an odd bounce optical image rotating system comprising a sequence of an odd number of reflective elements oriented in a manner which causes an entering beam of electromagnetic radiation to reflect from a first thereof onto the second thereof and from the second thereof onto the third thereof etc., such that said odd number of reflections cause a beam of electromagnetic radiation to emerge from the last odd number reflective element which is not significantly deviated or displaced from the locus of the input beam, even when the odd bounce optical image rotating element system is caused to rotate about an axis coincident with the locus of the beam of electromagnetic radiation. Said combination of substantially linear polarizer and odd bounce optical image rotating system serve to provide means for rotating the azimuthal angle of a substantially linearly polarized beam of electromagnetic radiation exiting said substantially linear polarizer without rotating the polarizer. Said combination of substantially linear polarizer and odd bounce optical Image rotating system finds application in ellipsometer and polarimeter and the like systems.

A basic present invention method of effecting and changing a polarization state of a beam of electromagnetic radiation comprises the steps of:
a. providing a system for effecting a polarization state change comprising in functional combination:
  a fixed position polarizer; and
  an odd bounce optical image rotating system comprising a sequence of an odd number of reflective elements oriented in a manner which causes an entering beam of electromagnetic radiation to reflect from a first thereof onto the second thereof and from the second thereof onto the third thereof etc., such that said odd number of reflections cause a beam of electromagnetic radiation to emerge from the last reflective element thereof which is not significantly deviated or displaced from the locus of the input beam, even when the odd bounce optical image rotating element system is caused to rotate about an axis coincident with the locus of the beam of electromagnetic radiation;
b. entering an electromagnetic beam to said polarizer;
c. stepwise or continuously rotating said odd bounce optical image rotating system about an axis coincident with the locus of the electromagnetic beam.

Said method of effecting and changing a polarization state of a beam of electromagnetic radiation preferably involves the odd bounce optical image rotating system being stepwise rotated about the axis coincident with the locus of the electromagnetic beam such that the polarization state of said beam of electromagnetic radiation is generally affected much as would be the case if the polarizer were so stepwise rotated.

Where data is to be obtained by directing a resulting beam into a detector, the odd bounce optical image rotating system can be caused to continuously rotate during data acquisition, however, preferred present invention practice is to cause another element, (eg. an analyzer or compensator), to be present and rotate during data acquisition while holding the polarizer and odd bounce optical image rotating system both motionless between stepped azimuthal angle changes.

Continuing, a present invention ellipsometer system typically comprises at least one means for continuously modifying a polarization state of a beam of electromagnetic radiation through a plurality of polarization states during use. The Polarizer and/or Analyzer can be caused to rotate as one option and when adopted results in Rotating Analyzer and Rotating Polarizer based systems. However, the preferred present invention provides that the odd bounce optical image rotating system be positioned between a stationary polarizer and analyzer, (preferably near the linear polarizer), and be operated as a means for sequentially step-wise modifying a polarization state of a beam of electromagnetic radiation through a plurality of polarization states, while a compensator, which is also present between the stationary polarizer and analyzer, is caused to continuously rotate, while a beam of electromagnetic radiation caused to pass therethrough. (Note, this does not exclude the possibility of providing and rotating more than one compensator). While the preferred present invention ellipsometer system can utilize essentially any Compensator, a preferred embodiment of the present invention provides that the compensator, which is mounted to allow continuous rotation about the locus of a beam of electromagnetic radiation caused to pass therethrough, be selected from the group of consisting of:
  a single element compensator;
  a compensator system comprised of at least two per se. zero-order waveplates (MOA) and (MOB), said per se. zero-order waveplates (MOA) and (MOB) having their respective fast axes rotated to a position offset from zero or ninety degrees with respect to one another, with a nominal value being forty-five degrees;
  a compensator system comprised of a combination of at least a first (ZO1) and a second (ZO2) effective zero-order wave plate, said first (ZO1) effective zero-order wave plate being comprised of two multiple order waveplates (MOA1) and (MOB1) which are combined with the fast axes thereof oriented at a nominal ninety degrees to one another, and said second (ZO2) effective zero-order wave plate being comprised of two multiple order waveplates (MOA2) and (MOB2) which are combined with the fast axes thereof oriented at a nominal ninety degrees to one another; the fast axes (FAA2) and (FAB2) of the multiple order waveplates (MOA2) and (MOB2) in said second effective zero-order wave plate (ZO2) being rotated to a position at a nominal forty-five degrees to the fast axes (FAA1) and (FAB1), respectively, of the multiple order waveplates (MOA1) and (MOB1) in said first effective zero-order waveplate (ZO1);
  a compensator system comprised of a combination of at least a first (ZO1) and a second (ZO2) effective zero-order wave plate, said first (ZO1) effective zero-order wave plate being comprised of two multiple order waveplates (MOA1) and (MOB1) which are combined with the fast axes thereof oriented at a nominal ninety degrees to one another, and said second (ZO2) effective zero-order wave plate being comprised of two multiple order waveplates (MOA2) and (MOB2) which are combined with the fast axes thereof oriented at a nominal ninety degrees to one another; the fast axes (FAA2) and (FAB2) of the multiple order waveplates (MOA2) and (MOB2) in said second effective zero-order wave plate (ZO2) being rotated to a position away from zero or ninety degrees with respect to the fast axes (FAA1) and (FAB1), respectively, of the multiple order waveplates (MOA1) and (MOB1) in said first effective zero-order waveplate (ZO1);
  a compensator system comprised of at least one zero-order waveplate, ((MOA) or (MOB)), and at least one effective zero-order waveplate, ((ZO2) or (ZO1) respectively), said effective zero-order wave plate, ((ZO2) or (ZO1)), being comprised of two multiple order waveplates which are combined with the fast axes thereof oriented at a nominal ninety degrees to one another, the fast axes of the multiple order waveplates in said effective zero-order wave plate, ((ZO2) or (ZO1)), being rotated to a position away from zero or ninety degrees with respect to the fast axis of the zero-order waveplate, ((MOA) or (MOB)).

Additional compensator systems, previously disclosed in patent application Ser. No. 08/997,311, (now U.S. Pat. No. 5,946,098), and CIP's therefrom, which compensators are specifically within the scope of application with the present invention, and can be included in the above identified selection group are:

a compensator system comprised of a first triangular shaped element, which as viewed in side elevation presents with first and second sides which project to the left and right and downward from an upper point, which first triangular shaped element first and second sides have reflective outer surfaces; said retarder system further comprising a second triangular shaped element which as viewed in side elevation presents with first and second sides which project to the left and right and downward from an upper point, said second triangular shaped element being made of material which provides reflective interfaces on first and second sides inside thereof; said second triangular shaped element being oriented with respect to the first triangular shaped element such that the upper point of said second triangular shaped element is oriented essentially vertically directly above the upper point of said first triangular shaped element; such that in use an input electromagnetic beam of radiation caused to approach one of said first and second sides of said first triangular shaped element along an essentially horizontally oriented locus, is caused to externally reflect from an outer surface thereof and travel along a locus which is essentially upwardly vertically oriented, then enter said second triangular shaped element and essentially totally internally reflect from one of said first and second sides thereof, then proceed along an essentially horizontal locus and essentially totally internally reflect from the other of said first and second sides and proceed along an essentially downward vertically oriented locus, then externally reflect from the other of said first and second sides of said first triangular shaped elements and proceed along an essentially horizontally oriented locus which is undeviated and undisplaced from the essentially horizontally oriented locus of said input beam of essentially horizontally oriented electromagnetic radiation even when said retarder is caused to rotate; with a result being that retardation is entered between orthogonal components of said input electromagnetic beam of radiation;

a compensator system comprised of, as viewed in upright side elevation, first and second orientation adjustable mirrored elements which each have reflective surfaces; said compensator/retarder system further comprising a third element which, as viewed in upright side elevation, presents with first and second sides which project to the left and right and downward from an upper point, said third element being made of material which provides reflective interfaces on first and second sides inside thereof; said third element being oriented with respect to said first and second orientation adjustable mirrored elements such that in use an input electromagnetic beam of radiation caused to approach one of said first and second orientation adjustable mirrored elements along an essentially horizontally oriented locus, is caused to externally reflect therefrom and travel along a locus which is essentially upwardly vertically oriented, then enter said third element and essentially totally internally reflect from one of said first and second sides thereof, then proceed along an essentially horizontal locus and essentially totally internally reflect from the other of said first and second sides and proceed along an essentially downward vertically oriented locus, then reflect from the other of said first and second orientation adjustable mirrored elements and proceed along an essentially horizontally oriented propagation direction locus which is essentially undeviated and undisplaced from the essentially horizontally oriented propagation direction locus of said input beam of essentially horizontally oriented electromagnetic radiation even when said compensator/retarder is caused to rotate; with a result being that retardation is entered between orthogonal components of said input electromagnetic beam of radiation;

a compensator system comprised of a parallelogram shaped element which, as viewed in side elevation, has top and bottom sides parallel to one another, both said top and bottom sides being oriented essentially horizontally, said retarder system also having right and left sides parallel to one another, both said right and left sides being oriented at an angle to horizontal, said retarder being made of a material with an index of refraction greater than that of a surrounding ambient; such that in use an input beam of electromagnetic radiation caused to enter a side of said retarder selected from the group consisting of: (right and left), along an essentially horizontally oriented locus, is Caused to diffracted inside said retarder system and follow a locus which causes it to essentially totally internally reflect from internal interfaces of both said top and bottom sides, and emerge from said retarder system from a side selected from the group consisting of (left and right respectively), along an essentially horizontally oriented locus which is undeviated and undisplaced from the essentially horizontally oriented locus of said input beam of essentially horizontally oriented electromagnetic radiation even when said retarder is caused to rotate; with a result being that retardation is entered between orthogonal components of said input electromagnetic beam of radiation;

a compensator system comprised of first and second triangular shaped elements, said first triangular shaped element, as viewed in side elevation, presenting with first and second sides which project to the left and right and downward from an upper point, said first triangular shaped element further comprising a third side which is oriented essentially horizontally and which is continuous with, and present below said first and second sides; and said second triangular shaped element, as viewed in side elevation, presenting with first and second sides which project to the left and right and upward from an upper point, said second triangular shaped element further comprising a third side which is oriented essentially horizontally and which is continuous with, and present above said first and second sides; said first and second triangular shaped elements being positioned so that a rightmost side of one of said first and second triangular shaped elements is in contact with a leftmost side of the other of said first and second triangular shaped elements over at least a portion of the lengths thereof; said first and second triangular shaped elements each being made of material with an index of refraction greater than that of a surrounding ambient; such that in use an input beam of electromagnetic radiation caused to enter a side of a triangular shaped element selected from the group consisting of: (first and second), not in contact with said other triangular shape element, is caused to diffracted inside said retarder and follow a locus which causes it to essentially totally internally reflect from internal interfaces of said third sides of each of said first and second triangular shaped elements, and emerge from a side of said triangular shaped element selected from the group consisting of: (second and first), not in contact with said other triangular shape element, along an essentially horizontally oriented locus which is undeviated and undisplaced from the essentially horizontally oriented locus of said input beam of essentially horizontally oriented electromagnetic radiation even when said retarder is caused to rotate; with a result being that retardation is entered between orthogonal components of said input electromagnetic beam of radiation;

a compensator system comprised of a triangular shaped element, which as viewed in side elevation presents with first and second sides which project to the left and right and downward from an upper point, said retarder system further comprising a third side which is oriented essentially horizontally and which is continuous with, and present below said first and second sides; said retarder system being made of a material with an index of refraction greater than that of a surrounding ambient; such that in use a an input beam of electromagnetic radiation caused to enter a side of said retarder system selected from the group consisting of: (first and second), along an essentially horizontally oriented locus, is caused to diffracted inside said retarder system and follow a locus which causes it to essentially totally internally reflect from internal interface of said third sides, and emerge from said retarder from a side selected from the group consisting of (second and first respectively), along an essentially horizontally oriented locus which is undeviated and undisplaced from the essentially horizontally oriented locus of said input beam of essentially horizontally oriented electromagnetic radiation even when said retarder system is caused to rotate; with a result being that retardation is entered between orthogonal components of said input electromagnetic beam of radiation; and a compensator system comprised of first and second Berek-type retarders which each have an optical axes essentially perpendicular to a surface thereof, each of which first and second Berek-type retarders has a fast axis, said fast axes in said first and second Berek-type retarders being oriented in an orientation selected from the group consisting of: (parallel to one another and other than parallel to one another); said first and second Berek-type retarders each presenting with first and second essentially parallel sides, and said first and second Berek-type retarders being oriented, as viewed in side elevation, with first and second sides of one Berek-type retarder being oriented other than parallel to first and second sides of the other Berek-type retarder; such that in use an incident beam of electromagnetic radiation is caused to impinge upon one of said first and second Berek-type retarders on one side thereof, partially transmit therethrough then impinge upon the second Berek-type retarder, on one side thereof, and partially transmit therethrough such that a polarized beam of electromagnetic radiation passing through both of said first and second Berek-type retarders emerges from the second thereof in a polarized state with a phase angle between orthogonal components therein which is different than that in the incident beam of electromagnetic radiation, and in a propagation direction which is essentially undeviated and undisplaced from the incident beam of electromagnetic radiation even when said retarder system is caused to rotate; with a result being that retardation is entered between orthogonal components of said input electromagnetic beam of radiation;

a compensator system comprised of first and second Berek-type retarders which each have an optical axes essentially perpendicular to a surface thereof, each of which first and second Berek-type retarders has a fast axis, said fast axes in said first and second Berek-type retarders being oriented other than parallel to one another; said first and second Berek-type retarders each presenting with first and second essentially parallel sides, and said first and second Berek-type retarders being oriented, as viewed in side elevation, with first and second sides of one Berek-type retarder being oriented other than parallel to first and second sides of the other Berek-type retarder; such that in use an incident beam of electromagnetic radiation is caused to impinge upon one of said first and second Berek-type retarders on one side thereof, partially transmit therethrough then impinge upon the second Berek-type retarder, on one side thereof, and partially transmit therethrough such that a polarized beam of electromagnetic radiation passing through both of said first and second Berek-type retarders emerges from the second thereof in a polarized state with a phase angle between orthogonal components therein which is different than that in the incident beam of electromagnetic radiation, and in a propagation direction which is essentially undeviated and undisplaced from the incident beam of electromagnetic radiation, said spectroscopic ellipsometer/polarimeter system further comprising third and forth Berek-type retarders which each have an optical axes essentially perpendicular to a surface thereof, each of which third and forth Berek-type retarders has a fast axis, said fast axes in said third and forth Berek-type retarders being oriented other than parallel to one another, said third and forth Berek-type retarders each presenting with first and second essentially parallel sides, and said third and forth Berek-type retarders being oriented, as viewed in side elevation, with first and second sides of one of said third and forth Berek-type retarders being oriented other than parallel to first and second sides of said forth Berek-type retarder; such that in use an incident beam of electromagnetic radiation exiting said second Berek-type retarder is caused to impinge upon said third Berek-type retarder on one side thereof, partially transmit therethrough then impinge upon said forth Berek-type retarder on one side thereof, and partially transmit therethrough such that a polarized beam of electromagnetic radiation passing through said first, second, third and forth Berek-type retarders emerges from the forth thereof in a polarized state with a phase angle between orthogonal components therein which is different than that in the incident beam of electromagnetic radiation caused to impinge upon the first side of said first Berek-type retarder, and in a direction which is essentially undeviated and undisplaced from said incident beam of electromagnetic radiation even when said retarder system is caused to rotate; with a result being that retardation is entered between orthogonal components of said input electromagnetic beam of radiation;

a compensator system comprised of first, second, third and forth Berek-type retarders which each have an optical axes essentially perpendicular to a surface thereof, each of which first and second Berek-type retarders has a fast axis, said fast axes in said first and second Berek-type retarders being oriented essentially parallel to one another; said first and second Berek-type retarders each presenting with first and second essentially parallel sides, and said first and second Berek-type retarders being oriented, as viewed in side elevation, with first and second sides of one Berek-type retarder being oriented other than parallel to first and second sides of the other Berek-type retarder; such that in use an incident beam of electromagnetic radiation is caused to impinge upon one of said first and second Berek-type retarders on one side thereof, partially transmit therethrough then impinge upon the second Berek-type retarder, on one side thereof, and partially transmit therethrough such that a polarized beam of electromagnetic radiation passing through both of said first and second Berek-type retarders emerges from the second thereof in a polarized state with a phase angle between orthogonal components therein which is different than that in the incident beam of electromagnetic radiation, and in a propagation direction which is essentially undeviated and undisplaced from the incident beam of electromagnetic radiation; each of which third and forth Berek-type retarders has a fast axis, said fast axes in said third and forth Berek-type retarders being oriented essentially parallel to one another but other than parallel to the fast axes of said first and second Berek-type retarders, said third and forth Berek-type retarders each presenting with first and second essentially parallel sides, and said third and forth Berek-type retarders being oriented, as viewed in side elevation, with first and second sides of one of said third and forth Berek-type retarders being oriented other than parallel to first and second sides of said forth Berek-type retarder; such that in use an incident beam of electromagnetic radiation exiting said second Berek-type retarder is caused to impinge upon said third Berek-type retarder on one side thereof, partially transmit therethrough then impinge upon said forth Berek-type retarder on one side thereof, and partially transmit therethrough such that a polarized beam of electromagnetic radiation passing through said first, second, third and forth Berek-type retarders emerges from the forth thereof in a polarized state with a phase angle between orthogonal components therein which is different than that in the incident beam of electromagnetic radiation caused to impinge upon the first side of said first Berek-type retarder, and in a direction which is essentially undeviated and undisplaced from said incident beam of electromagnetic radiation even when said retarder system is caused to rotate; with a result being that retardation is entered between orthogonal components of said input electromagnetic beam of radiation;

In addition, it is noted that a recent Patent to Aspnes describes application of a Berek-type Retarder which presents with an optical axis which is slightly deviated from a normal to the surface thereof, said Berek-type retarder being oriented so that a beam of electromagnetic radiation approaches along a normal to said surface, while the Berek-type Retarder is caused to rotate about said normal to said surface.

Further, while not required, the present invention benefits from Compensator(s) designed to provide relatively constant, achromatic Polarization State Modification effects over a Spectroscopic range of wavelengths.

The present invention will be better understood by reference to the Detailed Description Section of this Specification, in combination with the Drawings.

SUMMARY OF THE INVENTION

It is therefore a primary purpose and/or objective of the present invention to disclose a system which finds application in ellipsometer/polarimeter and the like systems, which system rotates the azimuthal angle of a linear polarization state of a beam of electromagnetic radiation-in a manner which does not significantly cause deviation of displacement thereof.

It is another purpose and/or objective of the present invention to disclose an odd bounce image rotating system which finds application in ellipsometer/polarimeter and the like systems, which odd bounce image rotating system rotates the azimuthal angle of a linear or partially linear, (substantially linear), polarization state of a beam of electromagnetic radiation in a manner which does not significantly cause deviation of displacement thereof.

It is yet another purpose and/or objective of the present invention to disclose a functional combination of a polarizer and an odd bounce image rotating system, wherein the polarizer provides a fixed position polarization state, and wherein the odd bounce image rotating system receives the polarized electromagnetic beam and sets the azimuthal angle of said polarization state.

It is another purpose and/or objective of the present invention to disclose application methodology of odd bounce image rotating systems in material system investigation systems, (eg. ellipsometer and polarimeter and the like systems).

Other purposes and/or objectives will become clear from a reading of the Specification and Claims.

DETAILED DESCRIPTION

Figure 1:
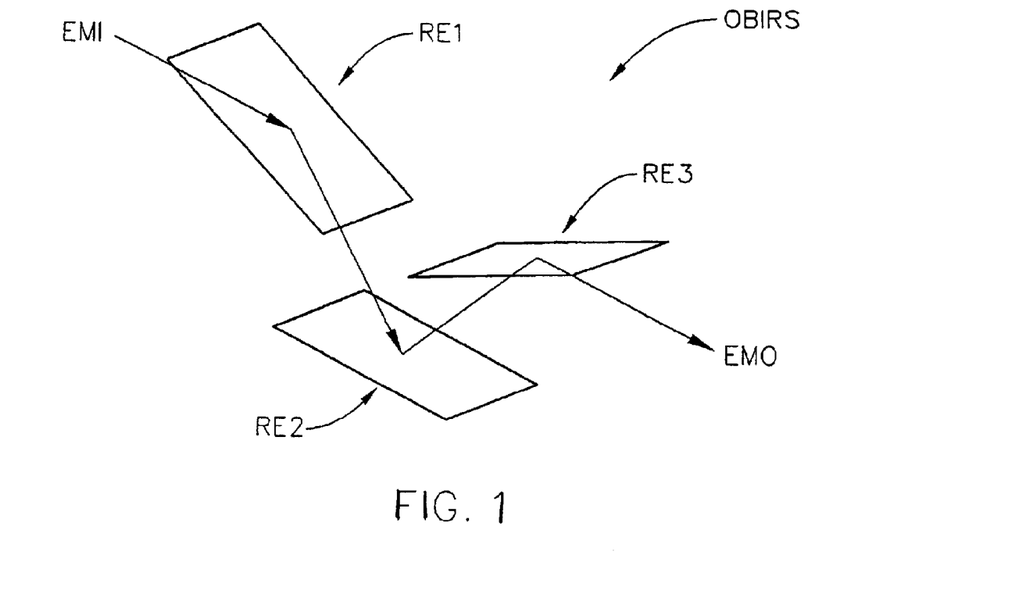
FIG. 1 demonstrates an odd bounce image rotating system comprising three (3) reflecting elements.

Turning now to FIG. 1, there is represented a three (3) bounce odd bounce image rotating system (OBIRS) comprising three (3) reflective elements (RE1), (RE2) and (RE3), oriented with respect to one another such that an input beam of electromagnetic radiation (EMI) exits as an output beam of electromagnetic radiation (EMO) without any deviation or displacement being entered into the locus thereof.

Figure 2:
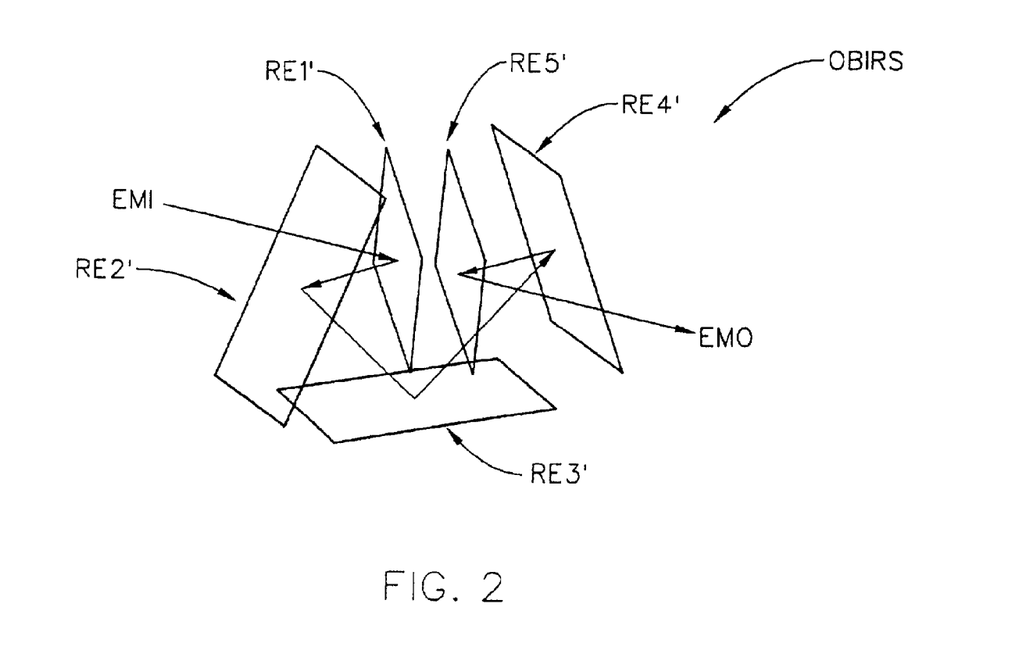
FIG. 2 demonstrates an odd bounce odd image rotating system comprising five (5) reflecting elements.

FIG. 2 demonstrates a five (5) bounce odd bounce image rotating system (OBIRS) wherein five reflective elements (RE1'), (RE2') (RE3'), (RE4') and (RE5') oriented with respect to one another such an input beam of electromagnetic radiation (EMI) exits as an output beam of electromagnetic radiation (EMO) without any deviation or displacement being entered into the locus thereof. Note generally that the angle of incidence of the (EMI) and (EMO) beams of electromagnetic radiation are nearer normal than is the case in the FIG. 1 three (3) bounce odd bounce image rotating system (OBIRS). This is beneficial in that the closer to normal the angle of incidence, the less aberration effects are entered to the beam. However, it is also to be appreciated that construction of the FIG. 2 system is more difficult than is construction of a FIG. 1 system.

Figures 3A, 3B, 3C:
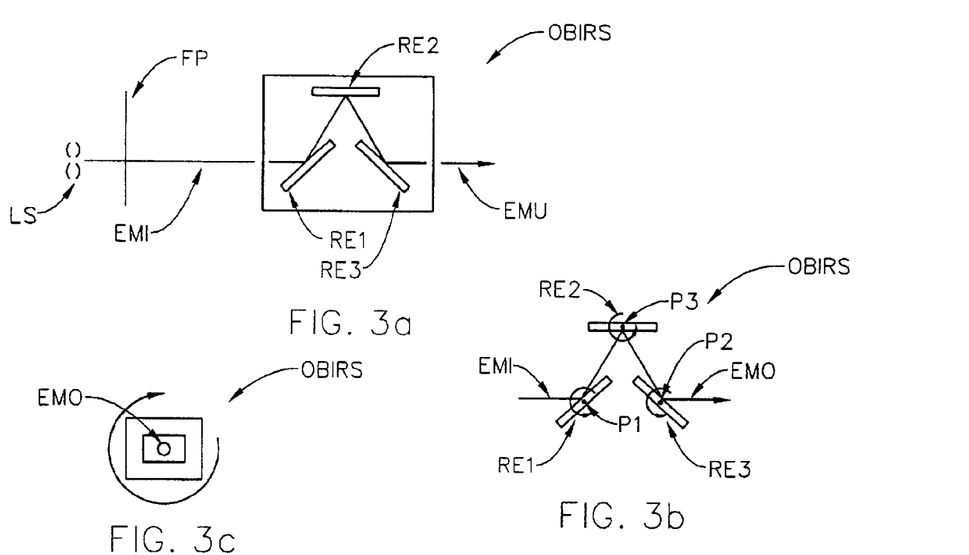
FIG. 3a demonstrates a combination fixed position polarizer and rotatable odd bounce image rotating system.
FIG. 3b shows that the reflective elements in the rotatable odd bounce image rotating system of FIG. 3a can be pivotally mounted.
FIG. 3c shows an end view of the rotatable odd bounce image rotating system of FIG. 3a is rotatable about the output electromagnetic beam.

FIG. 3a demonstrates a combination fixed position polarizer (FP) and rotatable odd bounce image rotating system (OBIRS) which in combination provide a means for providing a polarized beam of electromagnetic radiation and for controlling the azimuthal angle of the polarization, without the need to rotate the fixed polarizer (FP).

FIG. 3b demonstrates that the reflective elements (RE1), (RE2) and (RE3) can be mounted pivotally via pivots (P1), (P2) and (P3) to allow easy alignment, so that the input (EM1) and output (EMO) beams of electromagnetic radiation can be oriented along the same locus, without deviation and displacement effects causing the output (EMO) beam to exit along a different locus than along that input beam (EMI) enters.

Figures 3D, 3E:
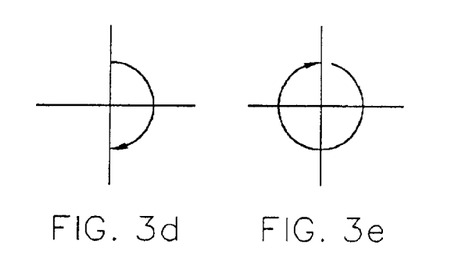
FIGS. 3d and 3e are included to demonstrate that a physical half rotation of an odd bounce optical image rotating system (OBIRS), (see FIG. 3d), around output electromagnetic beam (EMO), as viewed in FIG. 3c causes a full rotation of the linear polarization vector (see FIG. 3e).

FIGS. 3d and 3e are included to demonstrate that a physical half rotation of an odd bounce optical image rotating system (OBIRS), (see FIG. 3d), around output electromagnetic beam (EMO), as viewed in FIG. 3c causes a full rotation of the polarization vector (see FIG. 3e).

Figure 4:
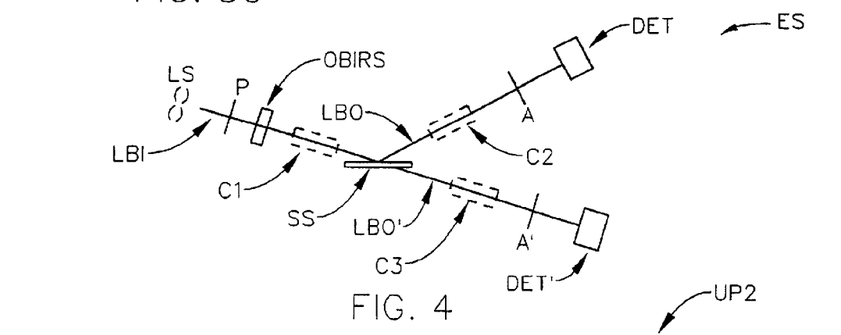
FIG. 4 demonstrates a rotating compensator ellipsometer system in which an odd bounce image rotating system is present after a fixed position linear polarizer.

FIG. 4 demonstrates a rotating compensator ellipsometer system in which an odd bounce image rotating system (OBIRS) is present immediately after a fixed polarizer (FP). Note also the relative orientation of a polychromatic electromagnetic radiation (LB1), optional compensator (C1) sample system (SS), optional compensator (C2), analyzer (A) and detector (DET) in the demonstrative upper reflective portion, (eg. follow electromagnetic beam (LBI) to (LBO). Further shown is a demonstrative transmissive portion comprised of optional compensator (C3), analyzer (A') and detector (DET'), (eg. follow electromagnetic beam (LBI) to (LBO). Preferred present invention practice has it that at least one of the compensators (C1), (C2) and (C3) will be present and caused to rotate during data acquisition and the odd bounce image rotating system (OBIRS) will be stepped to various azimuthal angle positions and set motionless during data acquisition, which the fixed linear polarizer (FP) and analyzer (A) (A') are held stationary. That is, the preferred present invention application is in a rotating compensator ellipsometer system, wherein the combination of the fixed polarizer and the odd bounce image rotating system (OBIRS) provide an effective rotatable polarizer. This is useful where a polarizer, (such as tipped wire grid plate polarizers used in the IR wavelength range), is difficult to rotate while maintaining alignment of the components therein and while avoiding deviation and displacement affects between input (EMI) and output (EMO) electromagnetic beams.

Figure 5:
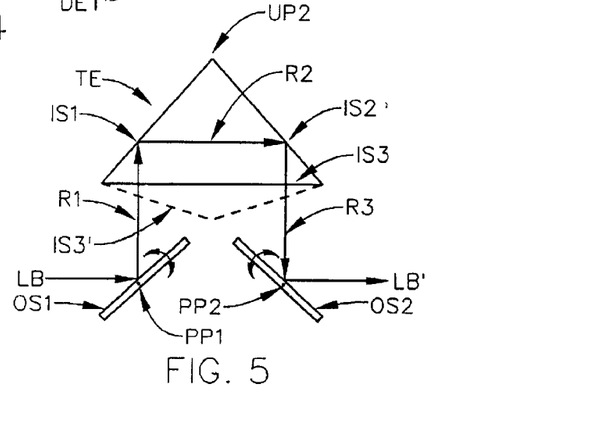
FIG. 5 demonstrates a preferred compensator (C) (C') C"), (see FIG. 4), for use in a rotating compensator ellipsometer system for application in the IR range of wavelengths.

FIG. 5 demonstrates a preferred compensator (C) (C') C") for use in a rotating compensator ellipsometer system for application in the IR range of wavelengths. The compensator system comprises, as shown in upright side elevation, first (OS1) and second (OS2) orientation adjustable mirrored elements which each have reflective surfaces. Note the adjustability enabling pivot (PP1) (PP2) mountings. Said compensator system further comprises a third element (TE) which, as viewed in upright side elevation presents with first (IS1) and second (IS2) sides which project to the left and right and downward from an upper point (UP2), said third element (TE) being made of material which provides reflective interfaces on first and second sides inside thereof. Said third element (TE) is oriented with respect to the first (OS1) and second (OS2) orientation adjustable elements such that in use an input electromagnetic beam of radiation (LB) caused to approach one of said first (OS1) and second (OS2) orientation adjustable mirrored elements along an essentially horizontally oriented locus, is caused to externally reflect therefrom upwardly vertically oriented, (see beam (R1)) then enter said third element (TE) and essentially totally internally reflect from one of said first and second sides thereof, then proceed along an essentially horizontal locus (see beam (R2)), and essentially totally internally reflect from the other of said first (OS1) and second (OS2) sides and proceed along an essentially downward vertically oriented locus, (see beam (R3)), then reflect, from the other of said first (OS1) and second (OS2) adjustable mirrored elements and proceed along an essentially horizontally oriented (LB') propagation direction locus which is essentially undeviated and undisplaced from the essentially horizontally oriented locus of said input beam of electromagnetic radiation even when said compensator is caused to rotate about the locus of the beam of electromagnetic radiation, with the result being that retardation is entered between orthogonal components of said input electromagnetic beam of radiation. Also shown are third element lower side (IS3), with indication that it can be shaped as shown by (IS3'), and retain functionality.

Figure 6A:
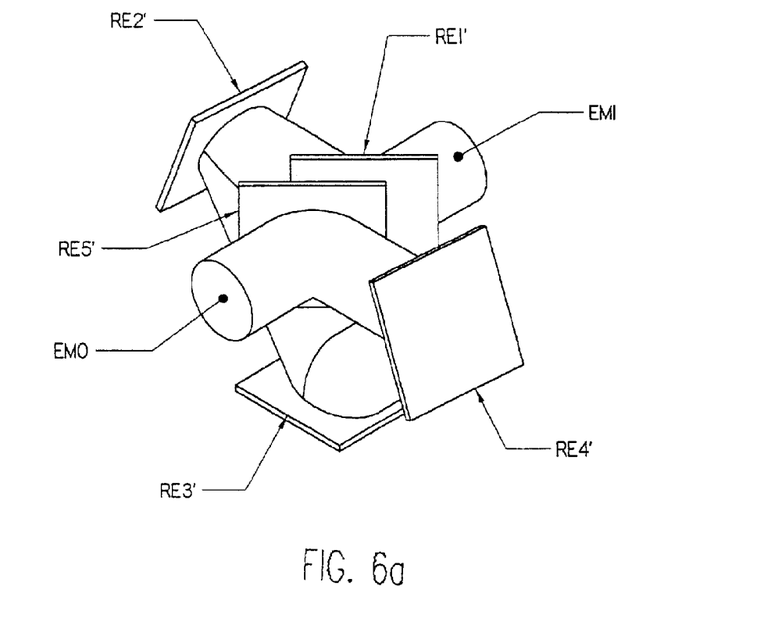
FIGS. 6a and 6b show a five (5) bounce odd bounce image rotating system (OBIRS), which should be beneficially compared to FIG. 2 to gain insight to how function and physical construction are related.
Figure 6B:
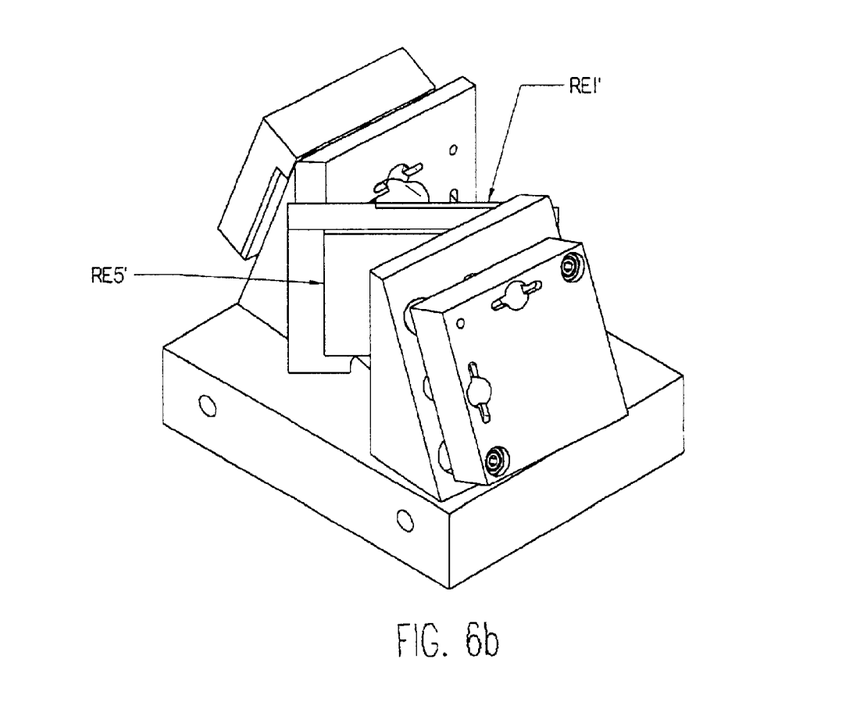

FIGS. 6a and 6b show a five (5) bounce odd bounce image rotating system (OBIRS), which should be beneficially compared to FIG. 2 to gain insight to how function and physical construction are related. Again, FIG. 2 shows five reflective elements (RE1'), (RE2') (RE3'), (RE4') and (RE5') oriented with respect to one another such an input beam of electromagnetic radiation (EMI) exits as an output beam of electromagnetic radiation (EMO) without any deviation or displacement being entered into the locus thereof. FIG. 6a identifies an input beam of electromagnetic radiation (EMI) exits from a five (5) bounce odd bounce image rotating system (OBIRS), as an output beam of electromagnetic radiation (EMO), (note that (EMI) and (EMO) are realistically shown as beams with a non-zero radius). The FIG. 6a positioning of the reflective elements (RE1'), (RE2') (RE3'), (RE4') and (RE5') lead to the reflections shown in FIG. 2. FIG. 6b further demonstrates physical construction of the FIG. 6a five (5) bounce odd bounce image rotating system (OBIRS).

Finally, it is to be understood that while preferred embodiments provide for application of a linear polarizer, the present invention can be used with a substantially linearly polarizing polarizer, or a polarizer which provides partially linearly polarization. In the Claims the term "polarizer" should then be interpreted broadly to mean preferably a linear polarizer, but including polarizers which provide partially linearly polarization.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the claims.

We claim:

1. In the context of a material system investigating system sequentially comprising:

source of electromagnetic radiation;
   polarizer;
   stage for supporting a sample system analyzer; and
   detector;

at least one odd bounce optical image rotating system being present between said polarizer and analyzer, said at least one odd bounce optical image rotating system comprising an odd number of at least three reflective elements oriented such that a beam of electromagnetic radiation provided by said source of electromagnetic radiation, after passing through said polarizer, interacts with each of said at least three reflective elements of said at least one odd bounce optical image rotating system and exits therefrom along a non-deviated non-displaced trajectory, said beam of electromagnetic radiation also interacting with a sample system placed on said stage for supporting a sample system, and said analyzer before entering said detector.

2. A material system investigating system as in claim 1, in which the at least one odd bounce optical image rotating system consists of a selection from the group consisting of three and five reflective elements.

3. A material system investigating system as in claim 2, in which the at least two of the reflective elements are adjustable such that the angle of incidence of a beam of electromagnetic radiation interacting therewith can be controlled.

4. A material system investigating system as in claim 1, which further comprises a compensator system present between said polarizer and analyzer.

5. A material system investigating system as in claim 4, in the compensator system comprises, as viewed in upright side elevation, first and second orientation adjustable mirrored elements which each have reflective surfaces; said compensator system further comprising a third element which, as viewed in upright side elevation presents with first and second sides which project to the left and right and downward from an upper point, said third element being made of material which provides reflective interfaces on first and second sides inside thereof; said third element being oriented with respect to the first and second orientation adjustable elements such that in use an input electromagnetic beam of radiation caused to approach one of said first and second orientation adjustable mirrored elements along an essentially horizontally oriented locus, is caused to externally reflect therefrom upwardly vertically oriented, then enter said third element and essentially totally internally reflect from one of said first and second sides thereof, then proceed along an essentially horizontal locus and essentially totally internally reflect from the other of said first and second sides and proceed along an essentially downward vertically oriented locus, then reflect from the other of said first and second adjustable mirrored elements and proceed along an essentially horizontally oriented propagation direction locus which is essentially undeviated and undisplaced from the essentially horizontally oriented locus of said input beam of electromagnetic radiation even when said compensator is caused to rotate about the locus of the beam of electromagnetic radiation, with the result being that retardation is entered between orthogonal components of said input electromagnetic beam of radiation.

6. A method of obtaining data from a material system investigating system comprising the steps of:

a. providing a material system investigating system which sequentially comprises:
      source of electromagnetic radiation;
      polarizer;
      stage for supporting a sample system analyzer; and
      detector;
      said material system investigating system further comprising at least one odd bounce optical image rotating system being present between said polarizer and analyzer, said at least one odd bounce optical image rotating system comprising an odd number of at least three reflective elements oriented such that a beam of electromagnetic radiation provided by said source of electromagnetic radiation, after passing through said polarizer, interacts with each of said at least three reflective elements of said at least one odd bounce optical image rotating system and exits therefrom along a non-deviated non-displaced trajectory, said beam of electromagnetic radiation also interacting with a sample system placed on said stage for supporting a sample system, and said analyzer before entering said detector;

b. placing a material system on said stage for supporting a sample system;

c. entering an electromagnetic beam to said polarizer from said source of electromagnetic radiation and causing it to impinge upon said material system;

d. detecting a beam of electromagnetic radiation exiting from said analyzer into said detector system.

7. A method of obtaining data as in claim 6, which further comprises the step of causing the at least one odd bounce optical image rotating system to stepwise or continuously rotate around the locus of the trajectory of the electromagnetic beam while practicing step d.

8. A system for effecting a polarization state change comprising in functional combination:

a fixed position polarizer; and
   an odd bounce optical image rotating system comprising a sequence of an odd number of reflective elements oriented in a manner which causes an entering beam of electromagnetic radiation to reflect from a first reflective element thereof onto a second thereof and from the second reflective element thereof onto a third reflective element thereof etc., such that said odd number of reflections cause a beam of electromagnetic radiation to emerge from the last reflective element without being significantly deviated or displaced from the locus of the input beam, even when the odd bounce optical image rotating system is caused to rotate about an axis coincident with the locus of the beam of electromagnetic radiation.

9. A method of effecting and changing a polarization state of a beam of electromagnetic radiation comprising the steps of:

a. providing a system for effecting a polarization state change comprising in functional combination:
   a fixed position polarizer; and
   an odd bounce optical image rotating system comprising a sequence of an odd number of reflective elements oriented in a manner which causes an entering beam of electromagnetic radiation to reflect from a first reflective element thereof onto a second thereof and from the second reflective element thereof onto a third reflective element thereof etc., such that said odd number of reflections cause a beam of electromagnetic radiation to emerge from the last reflective element with out being significantly deviated or displaced from the locus of the input beam, even when the odd bounce optical image rotating system is caused to rotate about an axis coincident with the locus of the beam of electromagnetic radiation;

b. entering an electromagnetic beam to said polarizer;

c. stepwise or continuously rotating said odd bounce optical image rotating system about an axis coincident with the locus of the electromagnetic beam.

10. A method of effecting and changing a polarization state of a beam of electromagnetic radiation as in claim 9 in which the odd bounce optical image rotating system is stepwise rotated about the axis coincident with the locus of the electromagnetic beam such that the polarization state of said beam of electromagnetic radiation is generally affected much as would be the case if the polarizer were so stepwise rotated.

* * * * *

UNITED STATES PATENT AND TRADEMARK OFFICE
CERTIFICATE OF CORRECTION

| | |
|---|---|
| PATENT NO. | : 6,795,184 B1 |
| APPLICATION NO. | : 09/963573 |
| DATED | : September 21, 2004 |
| INVENTOR(S) | : Herzinger et al. |

It is certified that error appears in the above-identified patent and that said Letters Patent is hereby corrected as shown below:

Column 17, line 26, add a --;-- after the word "system".

Column 18, line 22, add a --;-- after the word "system".

Signed and Sealed this

Twenty-sixth Day of August, 2008

JON W. DUDAS
*Director of the United States Patent and Trademark Office*